(12) United States Patent
Mitko

(10) Patent No.: US 8,362,419 B2
(45) Date of Patent: Jan. 29, 2013

(54) SECURITY APPARATUS

(76) Inventor: Sergey Mitko, Enschede (NL)

( * ) Notice: Subject to any disclaimer, the term of this patent is extended or adjusted under 35 U.S.C. 154(b) by 81 days.

(21) Appl. No.: 13/127,996

(22) PCT Filed: Oct. 25, 2009

(86) PCT No.: PCT/IB2009/054710
§ 371 (c)(1),
(2), (4) Date: May 6, 2011

(87) PCT Pub. No.: WO2010/052604
PCT Pub. Date: May 14, 2010

(65) Prior Publication Data
US 2011/0272574 A1  Nov. 10, 2011

(30) Foreign Application Priority Data
Nov. 6, 2008  (GB) .................................. 0820321.8

(51) Int. Cl.
*H01J 49/26* (2006.01)
(52) U.S. Cl. ....................................................... 250/286

(58) Field of Classification Search .................. 250/286, 250/287, 281, 282
See application file for complete search history.

(56) References Cited

U.S. PATENT DOCUMENTS

| | | | | |
|---|---|---|---|---|
| 4,445,038 A | * | 4/1984 | Spangler et al. | 250/382 |
| 6,995,361 B2 | * | 2/2006 | Kim et al. | 250/288 |
| 8,071,939 B2 | * | 12/2011 | Nuutinmaeki | 250/287 |

* cited by examiner

*Primary Examiner* — Kiet T Nguyen
(74) *Attorney, Agent, or Firm* — Graeser Associates International Inc; Dvorah Graeser

(57) ABSTRACT

An ion mobility spectrometer for analysing a gas is described which comprises a concentric arrangement of an inner ionization region 110, an annular reaction region 112 which surrounds the ionization region 110 and through which a gas to be analyzed is caused to flow continuously in the axial direction of the spectrometer, and an annular drift region 116 surrounding the reaction region through which ionised molecules of the gas to be analyzed flow in a radial direction towards a cylindrical detector 124 forming the outer wall of the drift region 116.

12 Claims, 3 Drawing Sheets

SECURITY APPARATUS

This Application claims priority from, and is a national phase of, PCT Application No. PCT/IB2009/054710, filed on Oct. 25, 2009, which claims priority from United Kingdom Application No. GB 0820321.8, filed on Nov. 6, 2008, all of which are hereby incorporated by reference as if fully set forth herein.

FIELD OF THE INVENTION

The present invention relates to an ion mobility spectrometer and is particularly concerned with security apparatus capable of detecting illegal substances especially in situations where they can access transport systems.

BACKGROUND OF THE INVENTION

The essential components of an ion mobility spectrometer are an ionisation source, a reaction region, a drift region and a detector. The principle on which ion mobility spectrometers operate is that charged ions accelerated by an electric field reach a terminal drift velocity when travelling through a gas such as air. The drift velocity is characteristic of the ions, being dependent upon such factors as their charge, size, mass and shape. As a result, if different ions are released at the same time into a drift region, across which an electric field is applied, they can be distinguished from one another by their time of arrival at a detector or collector electrode. Using this principle, one can analyse ionised gas samples to determine if they contain ionised molecules associated with illegal or dangerous substances, such as explosives, narcotics or highly combustible materials. As a result, this principle is well suited for use in security apparatus for preventing attacks by terrorists on public transport systems.

It is a known to take a small gas sample by enclosing a person in a portal. While the person is within the portal, short blasts of air are directed over the person to generate a small gas sample which is then analysed, for example with the aid of an ion mobility spectrometer. This approach suffers from some serious disadvantages, on account of the length of time it takes for each person to pass through the portal and on account of the lack of sensitivity of the equipment.

It is a disadvantage of the known portals that they are too slow, taking in excess of 30 seconds to allow a person through the portal, which is clearly unacceptable for a busy airport or underground transport system. This is because it takes some time for the gas sample created by the puffs of air to reach the spectrometer.

In accordance with a first aspect of the present invention, there is provided a security apparatus comprising a through passageway for admission of people or packages into a secure zone, and a fan for causing a gas stream drawn from the passageway to flow through an ion mobility spectrometer which is operative to analyse the gas stream repeatedly as it flows through the spectrometer.

In this aspect, the invention recognises that the vast majority of people using a public transport system will not be carrying any dangerous or illegal substances. A long passageway capable of containing several people, items of luggage, or larger items such as vehicles may therefore be tested for such substances continuously and whenever a positive reading is provided by the spectrometer only those people within the passage at that time need to be subjected to more rigorous examination, for example by testing each one separately in a portal that only allows one person through at a time.

In this case, the continuous gas flow will ensure that air that has been in contact with each passenger will have been analysed in the time taken for the passenger to cross the length of the passageway thereby avoiding the need to stop and examine each passenger separately.

In accordance with a second aspect of the invention, there is provided an ion mobility spectrometer for analysing a gas, comprising a concentric arrangement of an inner ionisation region, an annular reaction region which surrounds the ionisation region and through which a gas to be analysed is caused to flow continuously in the axial direction of the spectrometer, and an annular drift region surrounding the reaction region through which ionised molecules of the gas to be analysed flow in a radial direction towards a cylindrical detector forming the outer wall of the drift region.

In contrast with known ion mobility spectrometers which are designed to analyse a small gas sample, the spectrometer of the second aspect of the invention is designed to analyse a rapid continuous flow of gas and it is this feature that makes it particularly suitable for use in security apparatus.

Furthermore, conventional ion mobility spectrometers rely on an axial flow of ionised molecules towards a detector. This configuration places a limitation on the size of the detector and requires a complex system of electrodes to provide the necessary uniform acceleration field within the drift space. By contrast, the spectrometer of the invention can have a very large aperture and does not require any special steps to be taken to ensure a uniform radial field in the drift space. The concentric configuration allows multiple samples of ionised molecules to be introduced simultaneously into the drift space, all the samples being exposed to the same electric field and having exactly the same distance to travel before reaching the collector. In this way, the spectrometer can achieve an improved signal to noise ratio to achieve more reliable detection; this being of importance in security apparatus.

Another important parameter in judging the performance of an ion mobility spectrometer is its resolution, that is to say its ability to distinguish between ionised molecules having drift speeds that are close to one another.

It is possible to commence the measurement of the time that it takes for the charged molecules to traverse the drift region from the instant of their ionisation. In this case, the ionisation can be initiated by a corona discharge created by applying a sharp pulse to corona wires in the ionisation region. As an alternative, the drift region may be separated from the reaction region by a cylindrical ion shutter, in which case the ionisation region may having corona wires that are driven continuously.

To improve resolution, it is preferred to use an ion shutter that can be opened and closed very rapidly to introduce only a brief burst of ionised molecules into the drift space. The current pulse created by a particular constituent of the gas being analysed at the collector cannot be any shorter in time than the time during the ion shutter is open and if this time is prolonged then pulses caused by different gas molecules will merge into one another.

In a preferred embodiment of the invention, the ion shutter comprises a sheet of insulating material sandwiched between two layers of an electrically conductive material, the insulating sheet and the conductive layers being perforated by a matrix of holes. By applying voltages of suitable polarity to the two conductive layers, electric fields will be created in the holes that either permit the passage of ionised molecules or prevent it.

In order for the electric field created within each hole by the two conductors surrounding its opposite ends to be effective over the full diameter of the hole, it is important that the hole should have a diameter comparable in size to the thickness of the insulating sheet. Typically, the insulating sheet may have a thickness of 0.2 to 0.3 mm and the holes may have a diameter of around 0.5 mm. In practice the hole diameter and hole spacing will be a compromise. Larger diameters will require larger potential differences to close the shutter, while smaller diameter holes are difficult to achieve in practice especially since they need to cover a much of the area of the shutter as possible.

It is difficult to form an ion shutter in view of the large number of small holes that need to be made in the blank sheet from which the shutter is made. The holes are too small and numerous to be capable of being drilled mechanically. In experiments, it did not prove possible to use a laser alone to form the holes because it resulted in some of the holes being plated through, causing a short circuit between the two conductive layers.

A novel method of forming an ion shutter was therefore devised which comprised starting with a sheet of electrically insulating material sandwiched between two electrically conductive layers, chemically etching a matrix holes in each of the conductive layers, the holes on opposite sides of the electrically insulating sheet being in alignment with one another, and exposing the sheet to laser radiation to burn holes in the electrically insulating matter without short circuiting the electrically conductive layers.

By etching away the electrical conductor in the desired hole pattern prior to burning out the holes in the insulating material using a laser, it proved possible to achieve a high density of small holes (0.5 mm) without creating any short circuit between the conductive layers.

The choice of insulating material is important because a plastics material that is carbonised on exposure to a laser beam will itself short circuit the conductive layers on its opposite sides. It was found that PET was a good choice of material offering high strength and stability while leaving no conductive deposits when burn out by means of a laser.

Another factor affecting the resolution of an ion mobility spectrometer is the design of the ion collector. The reason for this is that a collector will being to sense a charged molecule while the molecule is still at some distance from it in the drift space. One way to avoid this is to place a grid at a fixed potential at a short distance from the collector which acts as a screen, the charge of an ionised molecule only being sensed by the collector after it has passed through the screen.

In an ion mobility spectrometer of the invention where the collector is a large cylinder, it is difficult to provide such a grid and to position it accurately in front of the collector.

To mitigate this problem, the collector may be formed of a flexible circuit board having two electrodes formed on it, each electrode comprising parallel interconnected conductive tracks that are interlaced with the tracks of the other electrode.

In use, two different bias voltages are applied to the two electrodes. When an ionised molecule is at a distance from the collector, each electrode will be equally affected by the charge and when the separately amplified signals from the two electrodes are subtracted from one another, the molecule will not produce a net output. However, is it comes close to the collector, each ionised molecule will be attracted only to the electrode with the opposite bias voltage to its own charge and in this way ionised molecules are only detected when they are at the point of impact with one of the collector electrodes.

In accordance with a further aspect of the invention, there is provided security apparatus for analysing gases passing over a person or a package to detect illegal or hazardous substances, the apparatus comprising a chamber sufficiently large to accommodate a person or package to be analysed, a recirculation passage connected in parallel with the chamber to form a closed circuit, a fan for continuously circulating a gas stream around the closed circuit and an ion mobility spectrometer arranged in the recirculation passage to analyse repeatedly the stream of gas recirculating through from the chamber.

This aspect of the invention differs from prior art proposals in that the ion mobility spectrometer does not analyse a small gas sample produced by a quick burst of air but a continuous gas stream. This in itself is equivalent to taking numerous discrete samples which will increase the reliability of the measurements. The fact that the gas stream is recirculated is important in that the analysed gas will pass over the suspect person or package several times, each time increasing the concentration of air borne substances to be detected.

This aspect of the invention is particularly suited for analysing shipping containers. Such containers have ventilation holes which will allow the containers to be analysed for forbidden substances without even the need to open them by simply connecting the recirculation passage containing the fan and the ion mobility spectrometer to two of the ventilation holes. The entire analysing equipment may be mounted on a gantry used to lift and move containers in a port, thereby enabling containers to be checked at the same time as they are being moved.

A problem that is encountered with any detector that analyses the composition of a gas and looks for traces of non-permitted substances is that some substances may not emit any ions or molecules for the detector to sense. Heating the intake air and taking steps to increase the scrubbing action of the air help may not always be sufficient.

In order to address this problem, there is provided in accordance with a still further aspect of the invention, a security apparatus having a chamber for receiving an article to be tested and a detector for analysing air which has passed through the chamber to detect if a non-permitted substance is present in the article, characterised in that means are provided for introducing into the air admitted into the chamber a dopant that reacts chemically with the non-permitted substance so as to increase or decrease the concentration within the air that has passed through the chamber of molecules to which the detector is sensitive.

Preferably, the apparatus comprises a second detector for analysing the air admitted into the chamber and means for comparing the results of analysis of the two detectors to sense any increase or decrease in the concentration of selected molecules on account of the passing of the air through the chamber. A detector constructed in the form of an ion mobility spectrometer as set forth above lends itself well for use in such an apparatus as the large area annular chamber surrounding a portal can be divided into two separate detectors one disposed upstream and the other downstream of the tube containing the person or article under test.

Such an apparatus can detect non-permitted substances not only from the molecules that they emit but also those that they absorb and those they generate when they react with dopants which may be specifically targeted.

The invention will now be described further, by way of example, with reference to the accompanying drawing, in which.

Figure 1:
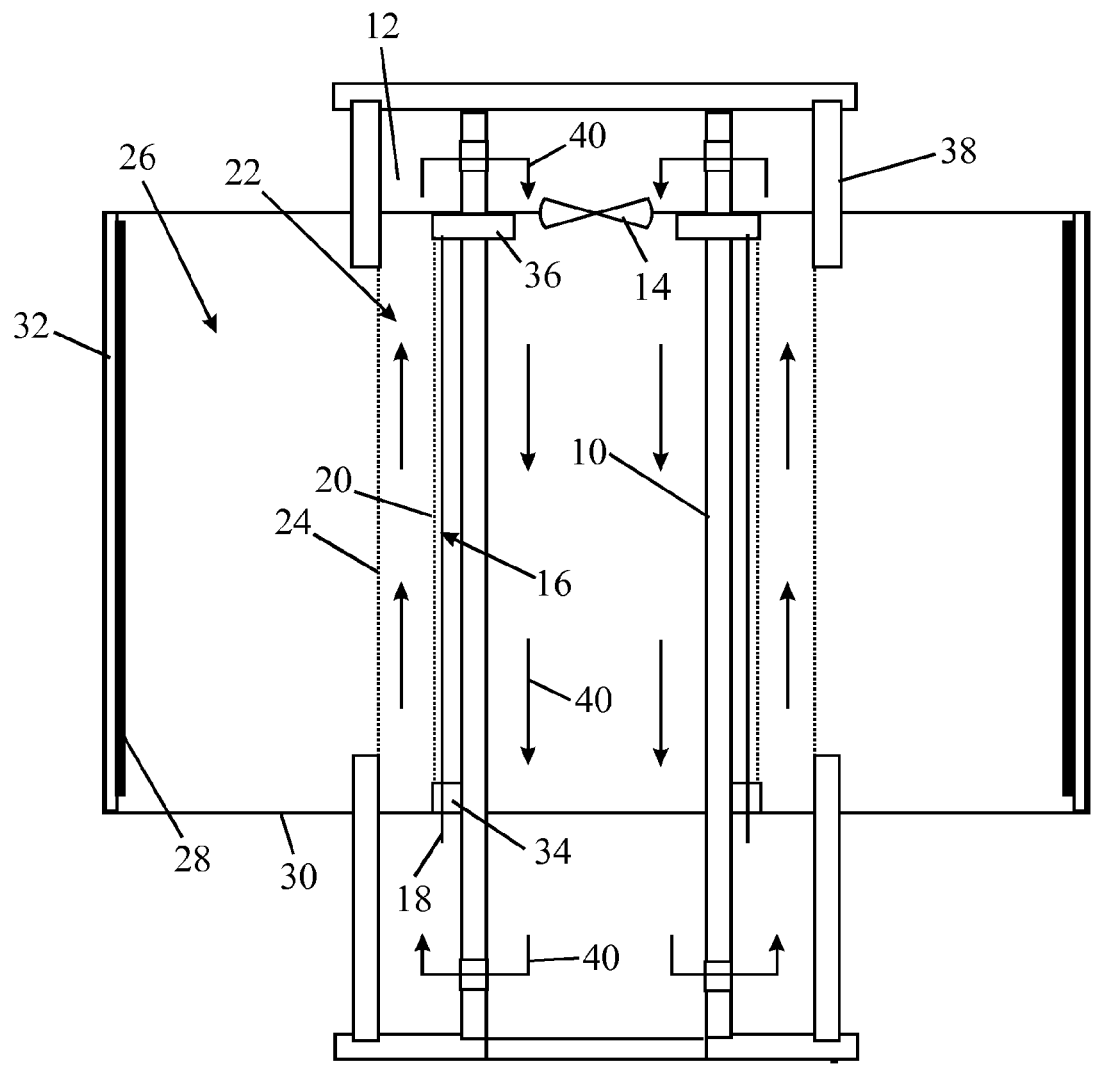
FIG. 1 is a section through a security apparatus of the invention.

FIG. 1 shows a portal for testing a single person or package. The portal comprises a vertical tube 10 having an entrance and an exit door (not shown). The tube 10 is surrounded by a chamber 12 and gas is circulated around the closed circuit consisting of the interior of the tube 10 and the chamber 12 by means of an air pump which blows or sucks air and is represented in the drawing as being a simple blower 14. The chamber 12 is formed within a casing 30 which is made entirely of metal to prevent interference with the operation of the ion mobility spectrometer which is contained within the chamber 12.

The ion mobility spectrometer is formed of an ionisation region 16 defined between corona discharge wires 18 and a first grid 20; a reaction region 22 defined between the first grid 20 and a second grid 24; and a drift region 26 defined between the second grid 24 and a detector or collector electrode 28. The electrode 28 is supported on the metal casing 30 of the chamber 12 by way of an insulating layer 32. The corona wires 18 and the grid 20 bars are mounted on insulating flanges 34 and 36 of the tube 10 while the second grid 24 is supported by a concentric split outer tube 38. Alternatively, both grids may be mounted on a plastic, stepped insulator.

In operation of the illustrated portal, a person stands within the tube 10 while the blower 14 is operated to circulate air over the person and through the chamber 12 as represented by the arrows 40. Because the air is constantly recirculated, it passes over the person within the portal several times, each time increasing the concentration in the circulating air of vapours of any substance carried by the person. The air may be heated to assist in the vaporising of substances to be detected. The gas is repeatedly analysed in the ion mobility spectrometer surrounding the tube 10 to provide an indication of whether the person is carrying non-permitted dangerous, explosive or other illegal substances.

Though the spectrometer is illustrated as being associated with a closed portal, it is alternatively possible for the tube 10 to be replaced by a corridor that is open at both ends for persons to walk through it. In this case, instead of analysing the vapours emitted from a single person, the ion mobility spectrometer will detect vapours from a group of people at the same time and should any non-permitted substance be detected then a warning can be issued for the individuals within the corridor at that time to be subjected to more thorough examination. The advantage of having an open corridor is that the flow of people into a secure zone will only be interrupted on the rare occasion that a person is detected to be carrying a non-permitted substance. This avoids the need to test every person separately which in certain instances is totally impracticable.

Within the ionisation region 16, the first grid 20 will be at a constant high potential of, for example 3 kV. Pulses of a higher voltage, for example 15 kV, are applied to the corona wires 18. Several corona wires distributed over the entire surface of the first grid 20 are commonly connected to a pulsed voltage supply to create a corona discharge over the entire area of the first grid 20. Each pulse applied to the corona wires 18 will result in air ions being injected into the interaction region 22 between the first grid 20 and the second grid 24, the latter being at a lower potential than the first grid 18, for the example 1 kV.

Within the interaction region between the first grid 20 and the second grid 24, the air ions collide with, and pass on their charge to, molecules of the gas in which non-permitted substances are to be detected and these ionised molecules will then pass through the second grid 24 and drift towards the detector electrode 28 across the drift region 26. The time of arrival of the ions at the detector electrode 28, referenced to the timing of the high-voltage pulses applied to the corona wires 18, is indicative of the ions passing through the drift region 26. The flow of ions will result in a current of the order of microamps being sensed at the detector electrode 28 and the current waveform, if displayed on an oscilloscope, will have peaks which coincide each with a respective ionised molecule present in the gas being analysed.

Because the corona wires 18 are pulsed continuously, for example at a frequency of 1 KHz, numerous consecutive samples are taken and analysed from the tube or corridor 10 which increases the reliability of the measurements.

The current flowing through the detector electrode can conveniently be analysed digitally. The signal may be converted by an analogue to digital converter into a stream of digits which are introduced into a shift register so that the currents caused by ions arriving at different times are stored in different locations in the register. The values stored during different measurement cycles can be analysed statistically to provide an indication of which ions are present and their relative concentrations. It is in this way possible to detect particular substances by their signature, that is to say the shape of their spectra.

If positive voltages are applied to the corona wires and grids then the spectrometer will be sensitive to positive ions and conversely negative voltages can be used to detect negatively charged molecules and ions. It is possible to alternate the polarity at a frequency lower than the repetition frequency of the pulses applied to the corona wires in order to detect both positive and negative ions.

Regardless of whether the gases to be analysed are recirculated through a closed tube or merely drawn from an open corridor, the illustrated ion mobility spectrometer will operate in the same manner and will provide the advantages of high sensitivity and reliability on account of the large area of all three regions.

In a portal in which air is drawn into a chamber containing a person or package and the air is discharged back into the ambient atmosphere, it is possible to divide the ion mobility spectrometer into two parts, one arranged upstream and the other downstream of the chamber in the direction of air flow. By analysing the difference between the output signals of the two parts of the spectrometer it is possible to compensate for background noise, in other words to disregard any signals caused by substances to be found in the ambient atmosphere, rather than emanating from the person or package within the chamber.

In a portal of this design, it is furthermore possible to dope the air stream with small harmless quantities of a chemical composition that will react chemically with substances to be detected. In this case, the difference between the two output signals of the parts of the spectrometer will not only indicate if vapours have been emitted by the person or package but also if vapours been absorbed by the person or package. Doping the intake air in this way can assist in identifying substances that do not vaporise easily. The dopant can be targeted at specific substances, being selected either because it is absorbed by the substance to be detected or because it reacts chemically with the substance to be detected to give off molecules that will be detected in the downstream part of the spectrometer.

Figure 2:
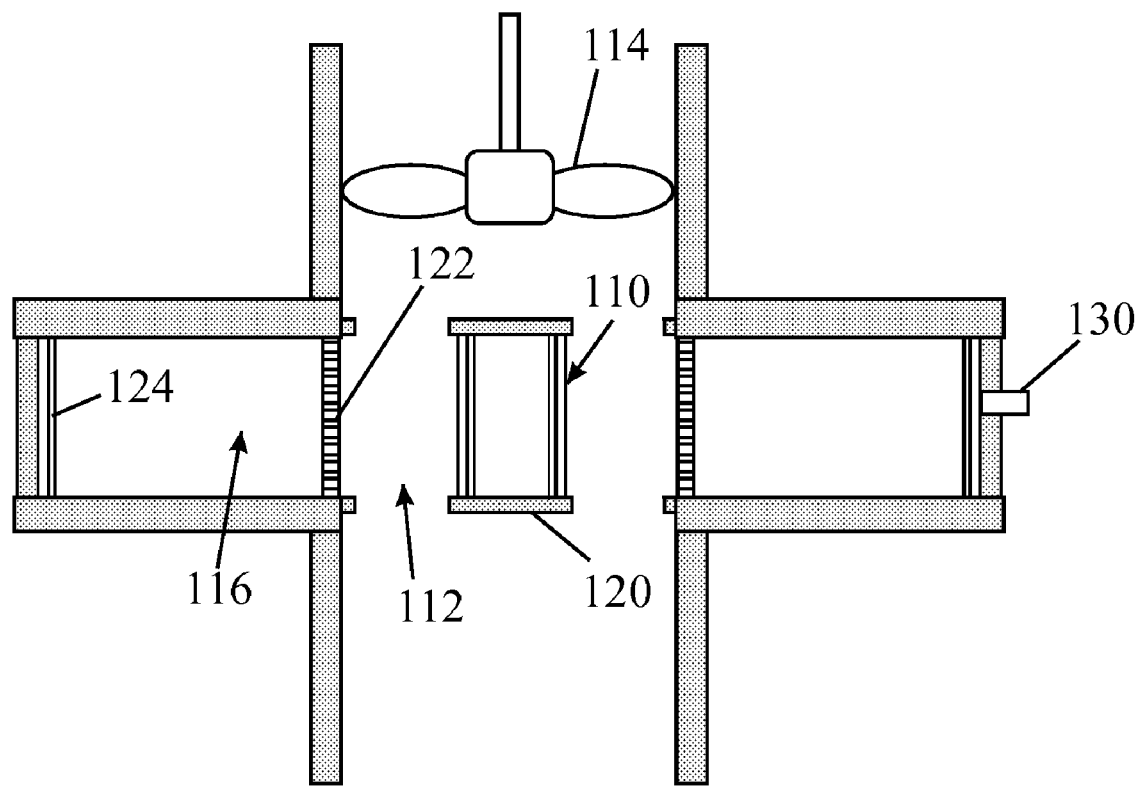
FIG. 2 is a section through an ion mobility spectrometer of a preferred embodiment of the invention.
Figure 3:
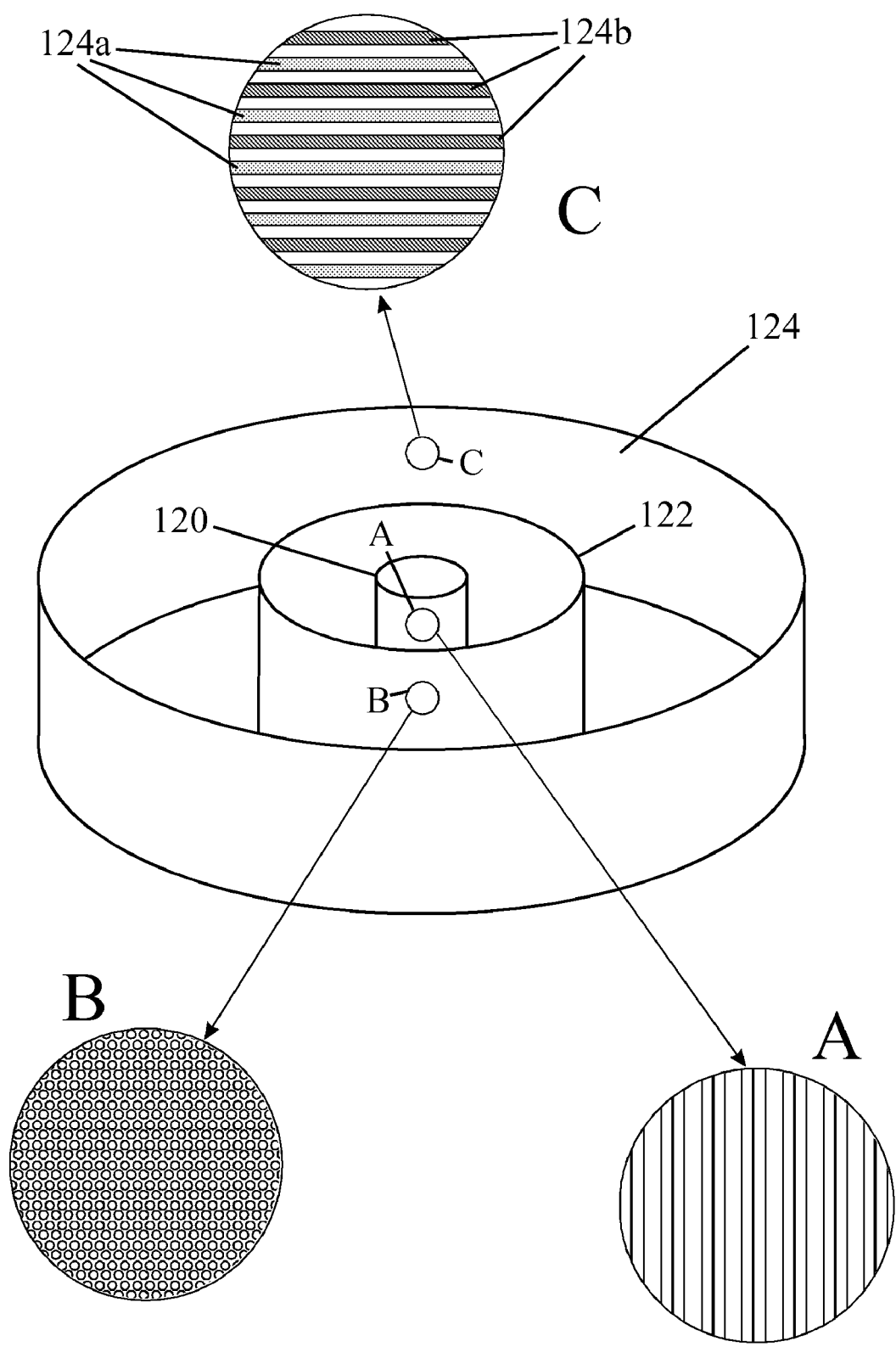
FIG. 3 is a schematic diagram which will be used to described in detail the construction of the ion mobility spectrometer of FIG. 2.

FIGS. 2 and 3 show an alternative construction of the ion mobility spectrometer. The spectrometer is shown in section in FIG. 2 which its essential components are shown diagrammatically in FIG. 3 along with detailed views showing the construction of these components.

In common with the spectrometer of FIG. 1, the spectrometer of FIGS. 2 and 3 has a cylindrical configuration in which ionised molecules are made to drift radially while the gas to be analysed flows continuously in an axial direction. Similarly, the spectrometer has an ionisation region 110, surrounded by a reaction region 112 through the gas to be analysed is sucked axially by means of a blower 114 and a drift region surrounding the reaction region 116. The air is again ionised by a corona discharge generated by an ionisation assembly 120 but this time the discharge is not pulsed but continuous and ensures that ionised molecules are continuously present in the reaction region 112. In this embodiment, however, the reaction region 114 is separated from the drift region 116 by an ion shutter 122 and the drift speed of ionised molecules is measured using the time that they are admitted into the drift region 116 by the shutter 122 to the time that they are sensed at the collector 124.

The surface of the ionisation assembly 120 is shown in the enlarged detailed A in FIG. 3. The assembly 120 comprises a tubular reference electrode with axially extending slits in its surface shown in thick lines in the detail A. centrally behind each slit there is a corona wire (shown in thinner lines) which is held at a potential of around 5 kV to 7 kV relative to the reference electrode.

The ion shutter shown in detail B comprises a thin sheet of PET (around 0.3 mm) with a copper layer on each side. A hexagonal matrix of holes with a diameter of around 0.5 mm is formed in the sheet making sure not to short circuit the two copper layers. This was achieved by first etching away the copper chemically, using the same process as is used in manufacturing double sided circuit boards and then burning holes in the PET using a laser.

The radially inner copper layer defines the end of the reaction region and is held a voltage of about 5 KV relative to the reference electrode of the ionisation assembly 120. The outer copper layer is held at a voltage of about 50 V above (or below depending on the ion polarity) the voltage of the inner copper layer to maintain the shutter closer. To open the shutter in order to admit charged molecules into the drift region 116 a short pulse of the opposite polarity is applied to the outer copper layer of the ion shutter 122.

The collector 124 has two electrode 124a, 124b shown in detail C of FIG. 3. Each electrode has parallel tracks connected to one another at one end and the tracks of each electrode are interlaced with the tracks of the other. Each of the electrodes is connected separately to an amplifier and the two amplified outputs area subtracted from one another to detect instant of impact of charges molecules.

In practice, the two electrodes of the collector 124 may for example have bias voltages of +50 V and −50 V applied to them. The steady voltage applied to the inner layer of the ion shutter 122 may typically be 10 kV. The voltage applied to the reference electrode of the ionisation assembly may be 15 kV and the voltage of the corona wires may be 22 kV. Negative values of the same magnitude may be used to detect molecules with a charge of the opposite polarity.

A nitrogen supply at a pressure very slightly above atmospheric pressure is connected to the outside of the drift region as represented by a connector 130 in FIG. 2. A very slow constant flow of nitrogen is introduced into the drift region 116. maintaining it at a slightly high pressure than the reaction region 112. This ensure that only charged molecules from the gas being analysed enter the drift region and also ensures that the drift speed is always measured in an atmosphere of substantially pure nitrogen at a known pressure. The nitrogen purging of the drift region is also effective in avoiding cross contamination between readings.

The invention claimed is:

1. An ion mobility spectrometer for analyzing a gas, comprising a concentric arrangement of
    an inner ionization region,
    an annular reaction region which surrounds the ionization region and is open at both axial ends to allow a continuous through flow of a gas to be analyzed in the axial direction of the spectrometer, and an annular drift region surrounding the reaction region through which ionized molecules of the gas to be analyzed flow in a radial direction towards a cylindrical detector forming an outer wall of the drift region.

2. An ion mobility spectrometer as claimed in claim 1, wherein the ionization region comprises means for generating a pulsed corona discharge.

3. An ion mobility spectrometer as claimed in claim 1, wherein the ionization region comprises means for generating a continuous corona discharge and an ion shutter is arranged between the reaction region and the drift region.

4. An ion mobility spectrometer as claimed in claim 3, wherein the ion shutter comprises a sheet of insulating material sandwiched between two layers of an electrically conductive material, the insulating sheet and the conductive layers being perforated by a matrix of holes.

5. An ion mobility spectrometer as claimed in claim 4, wherein the diameter of the holes is of the same order of magnitude as the thickness of the insulating sheet.

6. An ion mobility spectrometer as claimed in claim 4, wherein the ion shutter is manufactured by the method of providing a sheet of electrically insulating material sandwiched between two electrically conductive layers, chemically etching a matrix holes in each of the conductive layers, the holes on opposite sides of the electrically insulating sheet being in alignment with one another, and exposing the sheet to laser radiation to burn holes in the electrically insulating matter without short circuiting the electrically conductive layers.

7. An ion mobility spectrometer as claimed in claim 6, wherein the insulating material is PET (Polyethylene terephthalate).

8. An ion mobility spectrometer as claimed in claim 1, wherein the detector comprises a circuit board having two electrodes formed thereon, wherein each electrode comprises parallel conductive tracks that are interlaced with the tracks of the other electrode.

9. A security apparatus comprising a through passageway for admission of people or packages into a secure zone, and a fan for causing a gas stream drawn from the passageway to flow continuously through an ion mobility spectrometer for analysis by the spectrometer, wherein the ion mobility spectrometer comprises a concentric arrangement of an inner ionization region, an annular reaction region surrounding the ionization region and opening at both axial ends to allow the gas stream of the fan to flow continuously axially through the reaction region, and an annular drift region surrounding the reaction region through which ionized molecules of the gas to be analyzed flow in a radial direction towards a cylindrical detector delimiting the drift region.

10. A security apparatus for analyzing gases passing over a person or a package to detect illegal or hazardous substances, the apparatus comprising a chamber sufficiently large to accommodate a person or package to be analyzed, a recirculation passage connected in parallel with the chamber to form a closed circuit, a fan for continuously circulating a gas stream around the closed circuit and an ion mobility spectrometer arranged in the recirculation passage to analyze repeatedly the stream of gas recirculating through from the chamber, wherein the ion mobility spectrometer comprises a concentric arrangement of an inner ionization region, an annular reaction region surrounding the ionization region and open at both axial ends to allow the gas stream of the fan to flow continuously axially through the reaction region, and an annular drift region surrounding the reaction region through which ionized molecules of the gas to be analyzed flow in a radial direction towards a cylindrical detector delimiting.

11. A security apparatus having a chamber for receiving an article to be tested and an ion mobility spectrometer for analyzing air which has passed through the chamber to detect if a non-permitted substance is present in the article, wherein the ion mobility spectrometer comprises a concentric arrangement of an inner ionization region, an annular reaction region surrounding the ionization region and opening at both axial ends to allow a gas stream of a fan to flow continuously axially through the reaction region, and an annular drift region surrounding the reaction region through which ionized molecules of the gas to be analyzed flow in a radial direction towards a cylindrical detector delimiting, and wherein means are provided for introducing into the air admitted into the chamber a dopant that reacts chemically with the non-permitted substance so as to increase or decrease the concentration within the air that has passed through the chamber of molecules to which the detector is sensitive.

12. A security apparatus as claimed in claim 11, further comprising a second ion mobility spectrometer for analyzing the air admitted into the chamber and means for comparing the results of analysis of the two ion mobility spectrometers to sense any increase or decrease in the concentration of selected molecules on account of the passing of the air through the chamber.

* * * * *